United States Patent
Ugi et al.

(10) Patent No.: US 6,509,463 B1
(45) Date of Patent: Jan. 21, 2003

(54) ISOCYANOALKYLCARBONIC ACID DERIVATIVES, THE REACTION THEREOF IN ISOCYANIDE MULTICOMPONENT REACTIONS TO FORM SEC-AMIDO-ALKYLCARBONIC ACID DERIVATIVES, AND THOSE SEC-AMIDOALKYL-CARBONIC ACID DERIVATIVES

(75) Inventors: Ivar Ugi, Garching; Holger Bock; Thomas Lindhorst, both of Munich, all of (DE)

(73) Assignee: Ugichem GmbH, Hallbergmoos (DE)

( * ) Notice: Subject to any disclaimer, the term of this patent is extended or adjusted under 35 U.S.C. 154(b) by 0 days.

(21) Appl. No.: 09/630,766

(22) Filed: Aug. 2, 2000

Related U.S. Application Data

(62) Division of application No. 09/286,380, filed on Apr. 5, 1999, now Pat. No. 6,147,240, which is a continuation of application No. PCT/EP98/04622, filed on Jul. 23, 1998.

(30) Foreign Application Priority Data

Jul. 25, 1997 (DE) .......................... 197 31 893
Jul. 25, 1997 (DE) .......................... 197 32 176

(51) Int. Cl.$^7$ ............................. C07D 205/04
(52) U.S. Cl. ............... 540/200; 548/952; 548/953; 540/200; 540/362; 540/363; 540/364
(58) Field of Search ................. 548/952, 953; 558/418, 275, 276

(56) References Cited

U.S. PATENT DOCUMENTS 6,178,905 B1 * 2/2001 Hurst et al. ............... 530/329

FOREIGN PATENT DOCUMENTS

| | | |
|---|---|---|
| DE | 1 158 499 | 3/1962 |
| DE | 1 158 500 | 4/1962 |
| DE | 197 20 165 A1 | 5/1997 |
| DE | 197 20 216 A1 | 5/1997 |
| FR | 2 768 145 A1 * | 3/1999 |
| FR | 2 768 145 A1 * | 12/1999 |
| GB | 1005405 | 12/1963 |

OTHER PUBLICATIONS

Moiled with prior office Action mailed on Aug. 14, 2001.*
"Multicomponent reactions in organic chemistry" by Ivar Ugi, Alexander Domling and Werner Horl Endeavour New Series vol. 18, No. 3, 1994, pp. 115–122.

"The Formation of B–Lactam Derivatives and a C3–Symmetrical Heterocycle from 5,6–Dihydro–2H–1, 3–oxazines" by Konstantina Kehagia, Alexander Domling and Ivar Ugi Tetrahedron vol. 51, No. 1, pp.139–144, 1995.

"Einstufige Synthese von a–Hydroxysaure–amiden durch Abwandlung der Passerini–Reaktion" by Ilse Hagedorn and Ulrich Enholzer Insonitrile, vII, pp. 936–940.

"Ugi Reactions with trifunctional a–Amino Acids, Aldehydes, Isocyanides and Alcohols" by Ivar Ugi, Anton Demharter, Werner Horl and Thomas Schmid Tetrahedron vol. 52 No. 35, pp.11657–11664, 1996.

"Crosslinking of Aqueous Alginic Acid by Four Component Condensation with Inclusion Immobilization of Enzymes" by Stephan Konig and Ivar Ugi from Organisch–Chemisches Institut der Technischen Universitat Munchen, Lichtenbergstrabe 4, D–8046 Garching; A. Naturforsch 46b, 1261–1265 (1991) (in German).

* cited by examiner

Primary Examiner—Joseph K. McKane
Assistant Examiner—Kamal Saeed
(74) Attorney, Agent, or Firm—Frommer Lawrence & Haug, LLP; Ronald R. Santucci

(57) ABSTRACT

The present invention relates to compounds of the general formula I

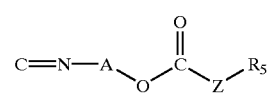

wherein A is a group of the formula

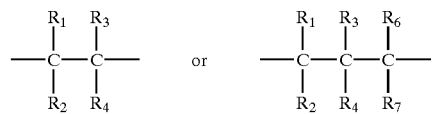

and Z is an O or S atom, to the further processing thereof to form novel sec-amidoalkylcarbonic acid derivatives and to those sec-amidoalkylcarbonic acid derivatives.

5 Claims, No Drawings

ISOCYANOALKYLCARBONIC ACID DERIVATIVES, THE REACTION THEREOF IN ISOCYANIDE MULTICOMPONENT REACTIONS TO FORM SEC-AMIDO-ALKYLCARBONIC ACID DERIVATIVES, AND THOSE SEC-AMIDOALKYL-CARBONIC ACID DERIVATIVES

This application is a division of U.S. patent application Ser. No. 09/286,380, filed Apr. 5, 1999 now U.S. Pat. No. 6,147,240 which is a continuation of International Application No. PCT/EP98/04622 filed on Jul. 23, 1998 and which designated the U.S.

The present invention relates to isocyanoalkylcarbonic acid derivatives, to the reaction therof in isocyanide multicomponent reactions to form sec-amidoalkylcarbonic acid derivatives, and to those sec-amidoalkylcarbonic acid derivatives.

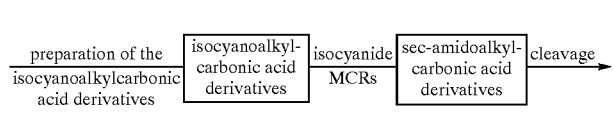

Many commercially interesting, organic substances (e.g. pharmacological active ingredients and natural substances) contain structural features that are derived from α-hydroxycarboxylic acid derivatives or α-aminocarboxylic acid derivatives. The synthesis of those substances is often a complex procedure. Using isocyanide multicomponent reactions (isocyanide MCRs), such as the Passerini reaction (P-3CR) and the various variants of the Ugi reaction, it is possible to prepare those complicated structural features in a simple manner [I. Ugi et al. in: *Comprehensive Organic Synthesis: Selectivity for Synthetic Efficiency*, Vol. II, B. M. Trost, C. H. Heathcock, Pergamon Press, Oxford, 1991].

In multicomponent reactions, three or more starting materials (components) can be reacted with one another simultaneously or almost simultaneously in a one-pot reaction without the need to work up intermediates. The group of isocyanide MCRs (one component is an isocyanide) includes, for example, the Passerini 3-component reaction (P-3CR); the Ugi 4-component reaction (U-4CR) [I. Ugi, *Angew. Chem.* 1962, 74, 9]; and the Ugi 5-centre 4-component reaction (U-5C-4CR) [I. Ugi et al., *Angew. Chem.* 1996, 108, 185] and the Ugi 4-component reaction with β-amino acids (U-4CR/β-AS) [I. Ugi et al., *Tetrahedron* 1995, 51, 139].

The products of those four types of reaction have secondary amide functions that are very difficult to convert into other derivatives, such as carboxylic acids and carboxylic acid esters, without the remainder of the molecule or any stereo-centres present being destroyed at the same time. The carbon atom of the secondary amide function that is formed originates from the isocyanide component used ($R^{Iso}$-NC).

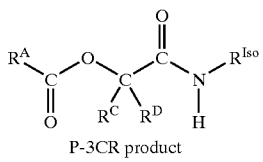

P-3CR product

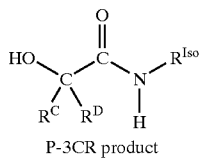

P-3CR product

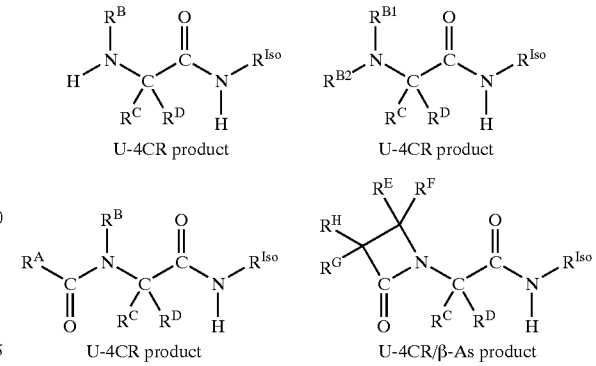

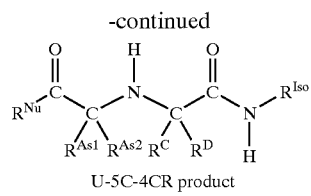

U-5C-4CR product

It is therefore a problem of the present invention to provide new isocyanide MCR products (sec-amidoalkylcarbonic acid derivatives), the secondary amide function of which can be converted into commercially interesting products (pharmacological sub-structures), such as α-hydroxycarboxylic acid derivatives or α-aminocarboxylic acid derivatives, under very mild reaction conditions.

A further problem of the present invention is to provide processes and intermediates for the preparation of the isocyanide MCR products.

The problem is solved by compounds (isocyanoalkylcarbonic acid derivatives) of the general formula I

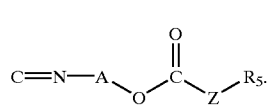

The isocyanoalkylcarbonic acid derivatives I are at least bifunctional molecules in which an isocyanide function and a carbonic acid derivative function are bonded to one another via a bridge A having a chain length of 2 or 3 carbon atoms. It is particularly significant that the compound I contains only one isocyanide function: the cleavage of sec-amidoalkylcarbonic acid derivatives that would be obtained from isocyanide MCRs with diisocyanoalkylcarbonic acid derivatives would result in non-uniform products.

In formula I

A is a group of the formula

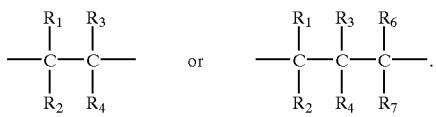

Z may be an O atom or a S atom, preferably an O atom.

The radicals $R_1$ to $R_4$ and, when present, $R_6$ and $R_7$ each have a maximum of 20 carbon atoms and are independently of one another H atoms, substituted or unsubstituted alkyl, alkenyl, alkynyl, alkaryl, aryl, alicyclic radicals, heteroalicyclic or heteroaryl radicals having up to 4 hetero atoms (hetero atoms are O, N, S); preferably those radicals each have a maximum of 15 carbon atoms, especially a maximum of 10 carbon atoms, and are independently of one another H atoms, substituted or unsubstituted alkyl, alkenyl, alkynyl, alicyclic or aryl radicals, more especially H atoms, substituted or unsubstituted methyl, ethyl, propyl, butyl, pentyl, hexyl, benzyl and cyclohexyl radicals, and most especially H atoms, methyl, ethyl, propyl, butyl, pentyl, hexyl, benzyl and cyclohexyl radicals.

Two of the radicals $R_1$ to $R_4$ and, when present, $R_6$ and $R_7$ that are separated from one another by up to two carbon atoms (such as, for example, the radicals $R_1$ and $R_2$, $R_3$ and $R_4$, $R_1$ and $R_3$ or $R_6$ and $R_7$, but not, for example, $R_1$ and R6, since the latter are separated from one another by three carbon atoms) may be constituents of a common ring system, the ring system comprising a substituted or unsubstituted alicyclic monocycle (5 to 8 ring atoms), a heteroalicyclic monocycle (5 to 8 ring atoms with 0, 1 or 2 hetero atoms [O, N, S]), an alicyclic bicycle (7 to 14 ring atoms) or a heteroalicyclic bicycle (7 to 14 ring atoms with up to 4 hetero atoms [O, N, S]), preferably a substituted or unsubstituted alicyclic monocycle (5 to 8 ring atoms) or an alicyclic bicycle (7 to 14 ring atoms), more especially a cyclopentyl, cyclohexyl, norbornyl or bornyl ring.

The radical $R_5$ has a maximum of 20 carbon atoms, preferably 15 carbon atoms, especially 10 carbon atoms, and is a substituted or unsubstituted alkyl, alkenyl, alkynyl, allyl, alkaryl, aryl, alicyclic radical, heteroalicyclic or heteroaryl radical having up to 4 hetero atoms (hetero atoms are O, N, S), preferably an allyl, benzyl, 2-bromoethyl, n-butyl, 2-chloroethyl, 1-chloroethyl, chloromethyl, ethyl, 1-(9-fluorenyl)-ethyl, 9-fluorenylmethyl, isobutyl, menthyl, 4-methoxycarbonylphenyl, 4-methoxyphenyl, methyl, 4-nitrobenzyl, 2-nitrophenyl, 4-nitrophenyl, 4,5-dimethoxy-2-nitrobenzyl, phenyl, 2,2,2-trichloro-tert-butyl, 2,2,2-trichloroethyl, vinyl, 4-methylphenyl, 4-fluorophenyl, 4-chlorophenyl, 4-bromophenyl, α-chloro-(trifluoromethyl) benzyl, 3-tert-butylphenyl, 2,4,6-trichlorophenyl, pentafluorophenyl, 2-(p-toluenesulfonyl)ethyl, diphenylmethyl, 2-(trimethylsilyl)ethyl, methoxymethyl, methylthiomethyl, (2-trimethylsilyl)ethoxymethyl, benzyloxymethyl or (2-methoxy)ethyloxymethyl radical.

If desired, the compounds of the formula I may be bonded to a solid phase (resin) via one or more of the radicals $R_1$ to $R_4$ and, when present, $R_6$ and $R_7$, also $R_5$ or Z. Suitable resins are, for example, any conventional resins that are used in organic solid phase synthesis, such as, for example, polystyrene/divinyl benzene, polyethylene glycol or polyethylene glycol/polystyrene resins.

The radicals $R_1$ to $R_4$ and, when present, $R_6$ and $R_7$ and also $R_5$, as well as ring systems formed from those radicals, may be substituted by one, two, three or more, preferably a maximum of one, of the following groups: halogen, tert-amino, nitro, cyano, ether, silyloxyalkyl, thioether, carboxylic acid ester, tert-carboxylic acid amide, carboxylic acid imide, silyl, sulfonic acid ester, sulfenic acid ester, sulfinic acid ester and tert-sulfonamido functions.

The substituents of the radicals $R_1$ to $R_4$ and, when present, $R_6$ and $R_7$ may, for example, increase the acidity of the H atom in the α-position to the isocyanide function and thus make it possible to use weak bases in the synthesis of the compound I. The choice of the radicals $R_1$ to $R_7$ is not essential for the suitability of the compound I for use in the isocyanide MCRs and the subsequent cleavage (see below), but they may be used, for example, to steer the solubility behaviour of the isocyanoalkylcarbonic acid derivatives or the cyclic urethanes formed in the cleavage.

A may especially be a group of the formula —C(CH$_3$)$_2$—CH$_2$—.

Preferred compounds of the formula I are:

(2-isocyano-2-methyl)-propyl-1-carbonic acid allyl ester, (2-isocyano-2-methyl)-propyl-1-carbonic acid benzyl ester, (2-isocyano-2-methyl)-propyl-1-carbonic acid (4-nitrobenzyl) ester, (2-isocyano-2-methyl)-propyl-1-carbonic acid ethyl ester, (2-isocyano-2-methyl)-propyl-1-carbonic acid phenyl ester, (2-isocyano-2-methyl)-propyl-1-carbonic acid (4-nitrophenyl) ester, (2-isocyano-2-methyl)-propyl-1-carbonic acid vinyl ester, (2-isocyano-2-methyl)-propyl-1-carbonic acid (2,2,2-trichloroethyl) ester, (2-isocyano-2-methyl)-propyl-1-carbonic acid (2-trimethyl-silyl-ethyl) ester, (2-isocyano-2-methyl)-propyl-1-carbonic acid methyl ester, (1-isocyano-2-methyl)-propyl-2-carbonic acid allyl ester, (1-isocyano-2-methyl)-propyl-2-carbonic acid benzyl ester, (1-isocyano-2-methyl)-propyl-2-carbonic acid (4-nitrobenzyl) ester, (1-isocyano-2-methyl)-propyl-2-carbonic acid ethyl ester, (1-isocyano-2-methyl)-propyl-2-carbonic acid phenyl ester, (1-isocyano-2-methyl)-propyl-2-carbonic acid (4-nitrophenyl) ester, (1-isocyano-2-methyl)-propyl-2-carbonic acid vinyl ester, (1-isocyano-2-methyl)-propyl-2-carbonic acid (2,2,2-trichloroethyl) ester, (1-isocyano-2-methyl)-propyl-2-carbonic acid (2-trimethyl-silyl-ethyl) ester, (1-isocyano-2-methyl)-propyl-2-carbonic acid methyl ester.

Also provided are processes for the preparation of compounds of the general formula I.

A process is characterised in that an isocyanoalkyl alcoholate anion CN—CR$_1$R$_2$—CR$_3$R$_4$—O$^-$ or CN—CR$_1$R$_2$—CR$_3$R$_4$—CR$_6$R$_7$—O$^-$ is reacted with a haloformic acid derivative X—CO—Z—R$_5$, for example in an aprotic solvent, such as THF, Et$_2$O, DME or CH$_2$Cl$_2$, to form a corresponding isocyanoalkylcarbonic acid derivative of the formula I, for example in accordance with the following scheme:

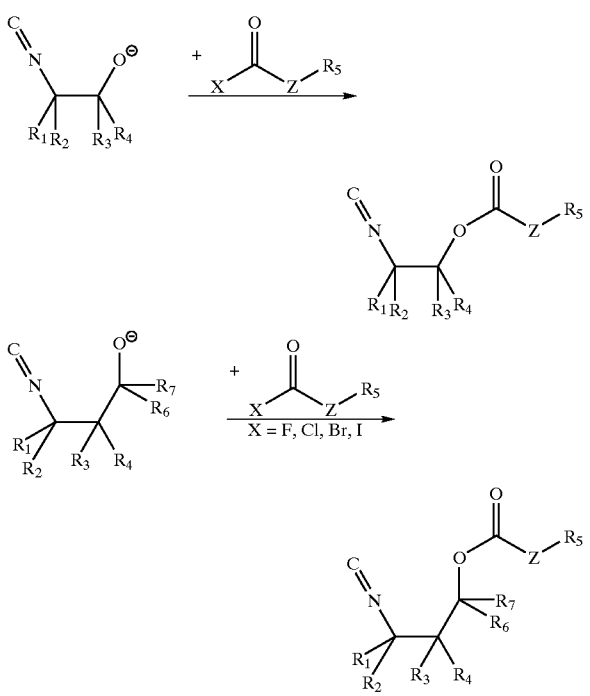

The isocyanoalkyl alcoholate anions may be prepared either from the corresponding isocyanoalkyl alcohols or from the cyclic imido esters (2-oxazoline or 2-oxazine) by reaction with a base (such as, for example, n-BuLi), as described in the literature [D. Hoppe, *Angew. Chem.* 1974, 86, 878].

The 2-oxazolines or 2-oxazines can readily be prepared from the corresponding 2-aminoethanols or 3-aminopropanols by reaction with formic acid [A. I. Meyers et al., *Tetrahedron* 1994, 50, 2297] or dimethylformamide dimethyl acetal [A. I. Meyers et al., *J. Org. Chem.* 1991, 56, 1961].

The required isocyanides may be prepared either from the corresponding amines by reaction with chloroform and strong bases, such as, for example, alkali metal hydroxide (carbylamine reaction) [I. Ugi et al in: *"Isonitrile Chemistry"*, I. Ugi (ed.), Academic Press, New York., 1971] or from the corresponding formamides by reaction with $POCl_3$ or phosgene [I. Ugi et al., *Angew. Chem.* 1965, 77, 492] in the presence of nitrogen bases.

A further process for the preparation of compounds of the general formula I is characterised in that a formamidoalkylcarbonic acid derivative $OCH-NH-CR_1R_2-CR_3R_4-O-CO-Z-R_5$ or $OCH-NH-Cr_1R_2-CR_3R_4-CR_6R_7-O-CO-Z-R_5$ is converted, for example, in an aprotic solvent, such as $CH_2Cl_2$, by removal of water into a corresponding isocyanoalkylcarbonic acid derivative of the formula I, for example in accordance with the following scheme.

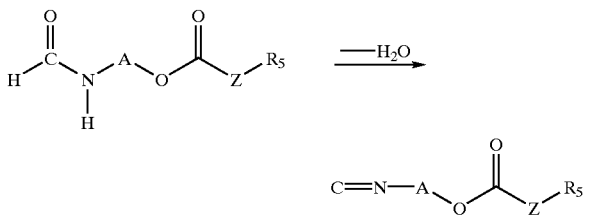

The removal of water may be effected, for example, by reaction with phosgene or di- or tri-phosgene or phosphorus oxychloride in the presence of nitrogen bases [I. Ugi et al., *Angew. Chem.* 1965, 77, 492].

The formamidoalkylcarbonic acid derivatives may be obtained by reaction of chloroformic acid derivatives with formamidoalkyl alcohols, which may in turn be prepared from the commercially available aminoalkyl alcohols by reaction with formic acid methyl ester.

Both processes are also suitable for the preparation of isocyanoalkylcarbonic acid derivatives that are bonded to a solid phase (resin) via one or more of the radicals $R_1$ to $R_4$ and, when present, $R_6$ and $R_7$, also $R_5$ or Z, for example to resins that are derivatised with a carbonyl function. Such resins are commercially available. In the process there are used, for example, resin-bonded chloroformic acid esters or isocyanides that can be prepared by derivatisation of OH-functionalised or SH-functionalised resins with phosgene [G. Skorna, I. Ugi, *Chem. Ber.* 1978, 111, 3965] or isocyanoalkylmethyl esters. The removal of water from correspondingly used resin-bonded formamides can also be carried out without problems [Mjalli A. M. M. et al., *Tetrahedron Lett.* 1996, 37, 1149].

All processes are also suitable for the preparation of chiral isocyanoalkylcarbonic acid derivatives.

Isocyanide Multicomponent Reactions

A multicomponent reaction is understood as being a reaction in which the product is formed from at least three different starting materials and contains substantial parts of those starting materials.

It is characteristic of isocyanide MCRs that in the course of such MCRs the two-bond carbon atom of the isocyanide function is converted in an intramolecular rearrangement, irreversibly and with energy being released, into a four-bond carbon atom of a secondary amide function. This constitutes the thermodynamic driving force of the isocyanide MCRs. This driving force has the effect that the intramolecular rearrangement takes place independently of the steric requirements of the substituents in question, so that virtually any substituents can be used. As a result, it is possible for an enormous range of acid, carbonyl, isocyanide and if applicable amine components to be used in the isocyanide MCRs. For that reason, isocyanide MCRs are the subject of intensive research in combinatorial chemistry where the aim is to prepare many different molecules in a one-pot synthesis [F. Balkenhohl, *Angew. Chem.* 1996, 108, 2463]. A large number of different Passerini and Ugi products have been prepared and described in the literature [I. Ugi, S. Lohberger, R. Karl in: *Comprehensive Organic Synthesis: Selectivity for Synthetic Efficiency*, Vol. II, B. M. Trost, C. H. Heathcock, Pergamon Press, Oxford, 1991; I. Ugi, *Angew. Chem.* 1962, 74, 9].

Using the isocyanide MCRs it is possible for complicated molecules to be synthesised simply and rapidly in a one-pot synthesis. The advantages over the customary multi-stage preparation methods are savings in time, savings in materials, higher yields with fewer secondary products and consequently reduced outlay for purification. The disadvantage of conventional isocyanide MCR products is that the secondary amide bond formed from the isocyanide cannot be modified or can be modified only in certain systems or only under drastic conditions.

The isocyanide MCRs can be carried out in a temperature range of from −90° C. to 90° C., preferably from 40° C. to 40° C. At low temperatures the MCRs proceed more slowly, while at too high a temperature the isocyanide may be destroyed.

Suitable solvents are any inert solvents that do not react or react only very slowly with the components used, such as, for example, lower alcohols, $CH_2Cl_2$, hexane, trifluoroethanol, THF or $CH_3CN$.

The reaction times may range from a few minutes to a few weeks.

The concentration range of the components may be from 0.01 molar to 10 molar, preferably from 0.1 to 2 molar. If the concentration is too low, the isocyanide MCRs proceed only very slowly, while too high a concentration may lead to secondary reactions. The components are preferably used in equimolar amounts, but it is also possible to use individual components in excess, since the resulting MCR products do not react further with the components used.

Also disclosed according to the invention are sec-amidoalkyl-carbonic acid derivatives of the formulae III to IX and processes for the preparation thereof.

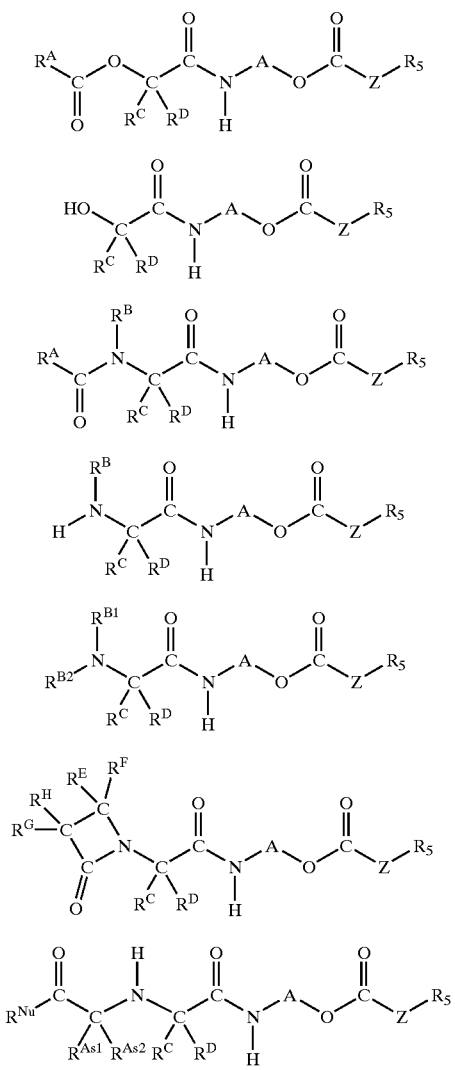

In the formulae III to IX, the radicals are defined as follows:

Z, A and the radical $R_5$ are as defined above;

the radicals $R^A$, $R^B$, $R^C$, $R^D$, $R^{As1}$, $R^{As2}$, $R^E$, $R^F$, $R^G$, $R^H$, $R^{B1}$ and $R^{B2}$ each have a maximum of 20 carbon atoms and are independently of one another H atoms or unsubstituted alkyl, alkenyl, alkynyl, alkaryl, aryl, alicyclic radicals, heteroalicyclic or heteroaryl radicals having up to 6 hetero atoms (hetero atoms are O, N, S) or are corresponding radicals that are substituted by one, two, three or more halogen, tertamino, nitro, cyano, carboxylic acid ester, carboxylic acid amide, carboxylic acid imide, alkyloxy, epoxy, boron, silyloxy, silyl, thio, sulfonic acid ester, sulfenic acid ester, sulfinic acid ester, sulfonamido, urethane or urea functions, or $R^B$ is a group of the formula OH, RR'N— (wherein R and R' may each independently of the other have the same definitions as $R^A$ but are independent thereof) or is a 1-aminocarbohydrate radical O-protected by $C_1$–$C_6$alkyl or by $C_1$–$C_6$alkylcarbonyl; preferably those radicals each have a maximum of 10 carbon atoms and are as defined above.

$R^{Nu}$ is a group of the formula HO—, $R^{Alk}$O— or $R^{Am1}R^{Am2}$N—, wherein $R^{Alk}$ is a methyl, ethyl, propyl, butyl, allyl or benzyl radical and $R^{Am1}$ and $R^{Am2}$ are $C_1$–$C_6$alkyl radicals, or $R^{Am1}$ and $R^{Am2}$ are constituents of a 5- or 6-membered cycloalkyl ring or 6-membered cycloalkyl ring having a further hetero atom (N, O).

Generally, the radicals $R^{s1A}$, $R^B$, $R^C$, $R^D$, $R^{As1}$, $R^{As2}$, $R^E$, $R^F$, $R^G$, $R^H$, $R^{B1}$, $R^{B2}$, R and R' may be substituted by any functional groups that do not react or react only very slowly with the functional groups of the isocyanide MCR components, see, for example, [I. Ugi, S. Lohberger, R. Karl in: *Comprehensive Organic Synthesis: Selectivity for Synthetic Efficiency*, Vol. II, B. M. Trost, C. H. Heathcock, Pergamon Press, Oxford, 1991; I. Ugi, *Angew. Chem.* 1962, 74, 9]. For example, aldehyde ketones may be used in the U-4CR, in which case when all the components are used in equimolar amounts only the aldehyde function reacts in the U-4CR as a result of its higher reactivity.

Sec.-amidoalkylcarbonic Acid Derivatives of the Formulae III and IV

In the Passerini reaction [M. Passerini, *Gazz. Chim. Ital.*, 1921, 51 (11); I. Hagedorn, U. Eholzer, *Chem. Ber.* 1965, 98, 936], an acid component, a carbonyl component (aldehyde or ketone) and an isocyanide component are used in a multicomponent reaction to synthesise α-acyloxyamides or α-hydroxyamides, for example in accordance with the following scheme.

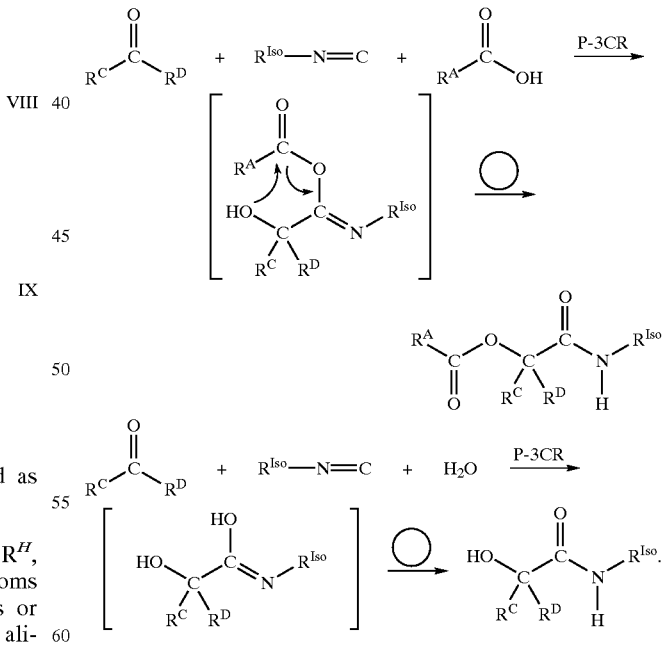

If a carbonyl component $R^C$—CO—$R^D$, the isocyanoalkylcarbonic acid derivative of the formula I and a carboxylic acid ($R^A$—COOH) as acid component are reacted in the P-3CR, the sec-amidoalkylcarbonic acid derivative III is formed; using water as acid component the Sec-amidoalkylcarbonic acid derivative IV is formed.

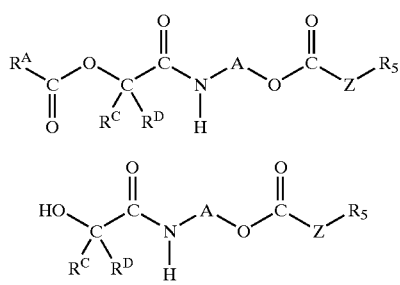

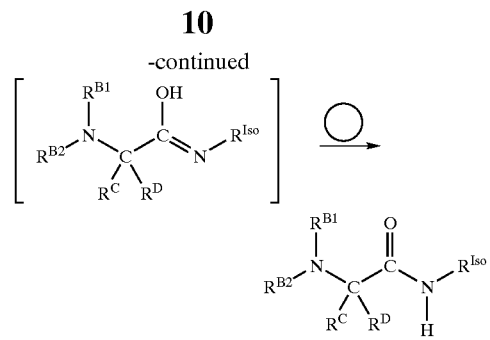

Preparation of Sec-amidoalkylcarbonic Acid Derivatives of the Formulae III and IV by Means of P-3CR A carboxylic acid $R^A$—COOH or water is reacted with a carbonyl component $R^C$—CO—$R^D$ and the isocyanoalkylcarbonic acid derivative of the formula I in a P-3CR. The reaction can be carried out, for example, as described in the literature [M. Passerini, *Gazz. Chim. Ital.*, 1921, 51 (11); I. Hagedorn, U. Eholzer, *Chem. Ber.* 1965, 98, 936].

Sec.-amidoalkylcarbonic Acid Derivatives of the Formulae V, VI and VII

In the U-4CR, the use of an acid component, for example carboxylic acid or water, a carbonyl component, an amine component (e.g. primary or secondary amine) and an isocyanide component yields α-aminoacylamides or α-aminoamides, for example in accordance with the following scheme:

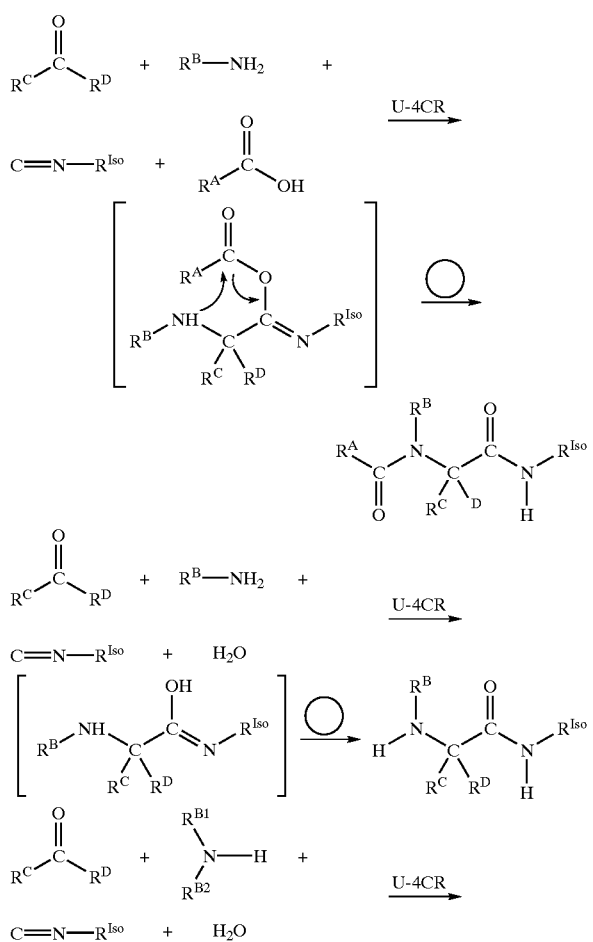

If a carbonyl component $R^C$—CO—$R^D$, the isocyanoalkylcarbonic acid derivative of the formula I, a carboxylic acid ($R^A$—COOH) and a primary amine ($R^B$—NH$_2$) are used in the U-4CR, the sec-amidoalkylcarbonic acid derivative V is formed; using water as acid component and a primary amine ($R^B$—NH$_2$), the sec-amidoalkylcarbonic acid derivative VI is formed. If a carbonyl component $R^C$—CO—$R^D$, the isocyanoalkylcarbonic acid derivative of the formula I, a secondary amine ($R^{B1}$—NH—$R^{B2}$) and water as acid component are used in the U-4CR, the sec-amidoalkylcarbonic acid derivative VII is formed.

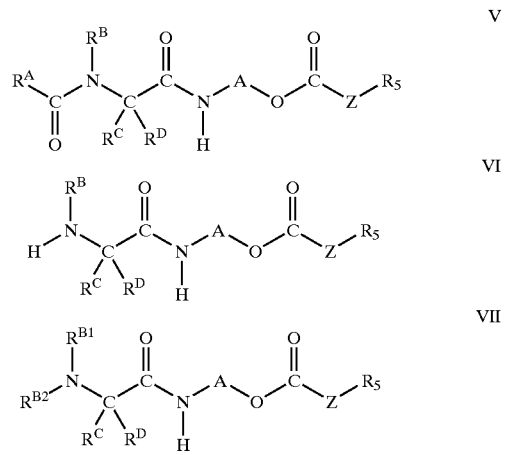

As amine components there may be used ammonia, primary amines, O-acylated or O-alkylated 1-aminocarbohydrates, hydroxylamines [NH$_2$OH] or hydrazines [H$_2$NNR(R')] and derivatives thereof.

As carbonyl components there are suitable both aldehydes (including sterically demanding aldehydes) and ketones (except for diarylketones). Occasionally pre-condensation of the imine is necessary.

The sec-amidoalkylcarbonic acid derivatives of the formulae V, VI and VII may be used, for example, to prepare N-acyl-α-amino acid derivatives, N-acyl-N-alkyl-α-amino acid derivatives or N,N'-dialkyl-α-amino acid derivatives.

Preparation of the Sec-amidoalkylcarbonic Acid Derivatives of the Formulae V, VI and VII by Means of U-4CR A carboxylic acid $R^A$—COOH or water is reacted with a carbonyl component $R^C$—CO—$R^D$, an amine component $R^B$—NH$_2$ or $R^{B1}$—NH—$R^{B2}$ and the isocyanoalkylcarbonic acid derivative of the formula I in an Ugi 4-component reaction. The reaction may be carried out, for example, as described in the literature [I. Ugi et al., *Chem. Ber.* 1961, 94, 2802].

Monocyclic Sec-amidoalkylcarbonic Acid Derivatives of the Formula VIII

The synthesis of monocyclic sec-amidoalkylcarbonic acid derivatives of the formula VIII by means of U-4CR/β-AS represents a variant of the U-4CR in which both the amine component and the acid component are present in a single starting material, a β-amino acid. The β-amino acid is reacted with a carbonyl component and an isocyanide component in a U-4CR/β-AS, for example in accordance with the following scheme:

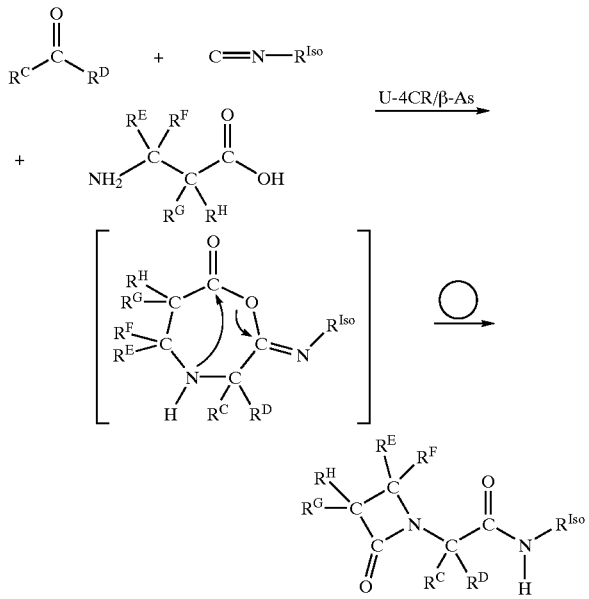

In that reaction, when a carbonyl component $R^C$—CO—$R^D$, the isocyanoalkylcarbonic acid derivative of the formula I and a β-amino acid $H_2N$—$CR^ER^F$—$CR^GR^H$—COOH are used, the sec-amidoalkylcarbonic acid derivative VIII is formed as reaction product.

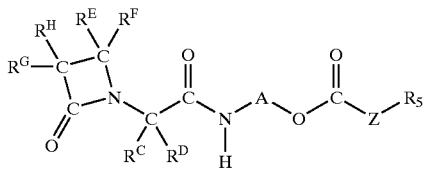

VIII

Preparation of Monocyclic Sec-amidoalkylcarbonic Acid Derivatives of the Formula VIII by Means of U-4CR/β-As A β-amino acid $H_2N$—$CR^ER^F$—$CR^GR^H$—COOH is reacted with a carbonyl component $R^C$—CO—$R^D$ and the isocyanoalkylcarbonic acid derivative of the formula I in a U-4CR/β-As. The reaction may be carried out, for example, as described in the literature [I. Ugi et al., *Tetrahedron* 1995, 51, 139].

Sec.-amidoalkylcarbonic Acid Derivatives of the Formula IX

The U-5C-4CR is a well-known variant of the U-4CR and is used for the preparation of 1,1'-iminodicarboxylic acid derivatives [W. Hörl, Dissertation, Technische Universität München, 1996]. In the U-5C-4CR, an α-amino acid, a carbonyl component, an isocyanide component and a nucleophile, which may be an alcohol, a secondary amine or water, are reacted, for example, according to the following scheme:

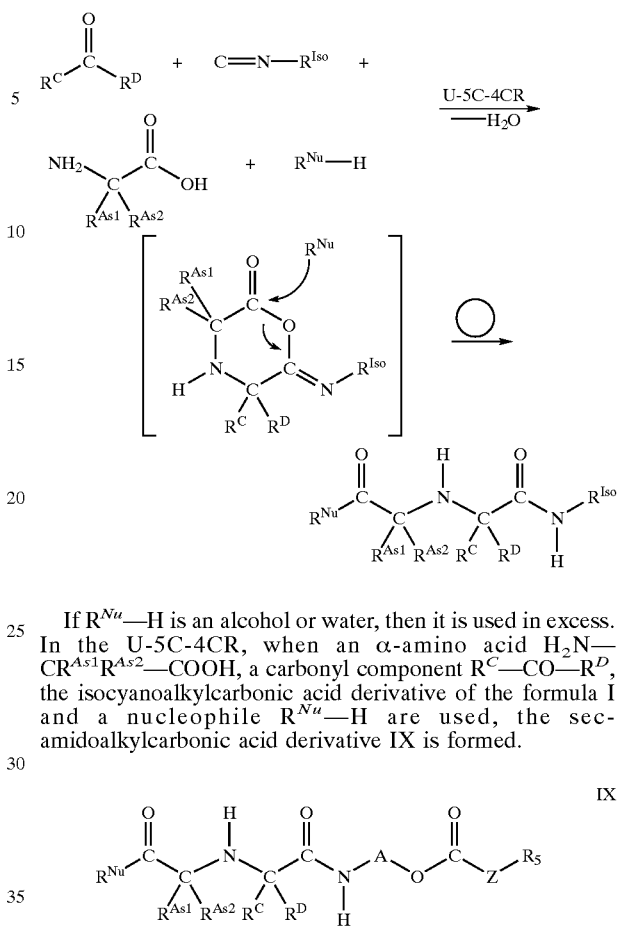

If $R^{Nu}$—H is an alcohol or water, then it is used in excess. In the U-5C-4CR, when an α-amino acid $H_2N$—$CR^{As1}R^{As2}$—COOH, a carbonyl component $R^C$—CO—$R^D$, the isocyanoalkylcarbonic acid derivative of the formula I and a nucleophile $R^{Nu}$—H are used, the sec-amidoalkylcarbonic acid derivative IX is formed.

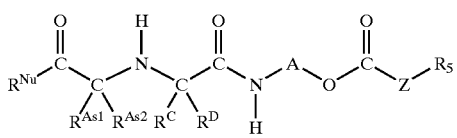

IX

Preparation of Sec-amidoalkylcarbonic Acid Derivatives of the Formula IX by Means of U-5C-4CR An α-amino acid $H_2N$—$CR^{As1}R^{As2}$—COOH is reacted with a carbonyl component $R^C$—CO—$R^D$, the isocyanoalkylcarbonic acid derivative of the formula I and a nucleophile $R^{Nu}$—H in an Ugi-5C-4CR. The reaction may be carried out, for example, as described in the literature [I. Ugi et al., *Tetrahedron*, 1996, 52, 11657].

If, for example, $R^{NU}$—H is an alcohol, then an α-amino acid, a carbonyl component and the isocyanoalkylcarbonic acid derivative I are dissolved or suspended in an alcohol, which is the solvent and the nucleophile simultaneously, and stirred. When the reaction is complete, the solvent is removed and, if necessary, the reaction product is purified.

If, for example, $R^{Nu}$—H is a secondary amine, then an α-amino acid, a carbonyl component, the isocyanoalkylcarbonic acid derivative I and a secondary amine are dissolved or suspended in a solvent/water mixture, such as, for example, a THF/$H_2O$ mixture, and stirred. When the reaction is complete, the solvent is removed and, if necessary, the reaction product is purified.

If, for example, $R^{NU}$—H is water, then an α-amino acid, a carbonyl component and the isocyanoalkylcarbonic acid derivative I are dissolved or suspended in a solvent/water mixture, such as, for example, a THF/$H_2O$ mixture, and stirred. When the reaction is complete, the solvent is removed and, if necessary, the reaction product is purified. Cleavage of the Secondary Amide Bond of the Sec-amidoalkylcarbonic Acid Derivatives of the Formulae III to IX It is also possible for the novel sec-amidoalkylcarbonic acid derivatives of the formulae III to IX to be converted without difficulty into α-hydroxycarboxylic acid derivatives or α-aminocarboxylic acid derivatives by reaction with a base.

By reaction of the sec-amidoalkylcarbonic acid derivatives with a base, the secondary amide proton is abstracted. Suitable bases are, for example, mild, non-nucleophilic bases, such as, for example, potassium tert-butanolate, alkali metal hydroxide, alkali metal hydride or nitrogen bases, such as lithium diisopropylamine or 1,5-diazabicyclo-[4.3.0]non-5-ene, for example in an aprotic solvent, such as, for example, THF, Et$_2$O or CH$_2$Cl$_2$. The reaction may be carried out at temperatures of from −80° C. to 80° C. By subsequent intramolecular ring closure, for example in accordance with the following scheme, there are prepared primary cleavage products X that have a cyclic N-acylurethane function.

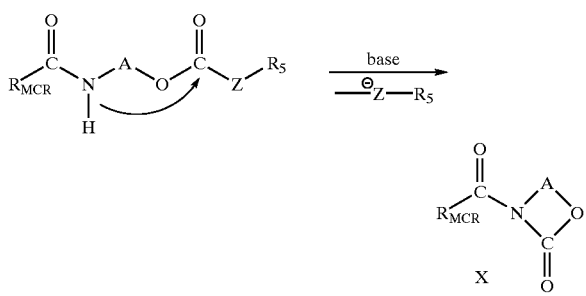

The radical R$_{MCR}$ defines the structures that are synthesised by the P-3CR, the U-4CR, the U-4CR/β-As and the U-5C-4CR. In the ring closure, Z—R$_5$ is removed in the form of an alcoholate or thiolate anion. The further course of the reaction is dependent on the structure of R$_5$. If R$_5$ is a radical that reduces the nucleophilicity of the Z function (e.g. an electrophilic radical, such as, for example, a phenyl radical), then X is capable of being isolated. If R$_5$ is a radical that increases the nucleophilicity of the Z function (e.g. an electron-donating radical, such as, for example, an alkyl radical), then X is not capable of being isolated, but reacts in situ with the alcoholate or thiolate formed by the intramolecular ring closure to yield the corresponding ester or thioester (R$_{MCR}$—CO—Z—R$_5$), for example in accordance with the following scheme.

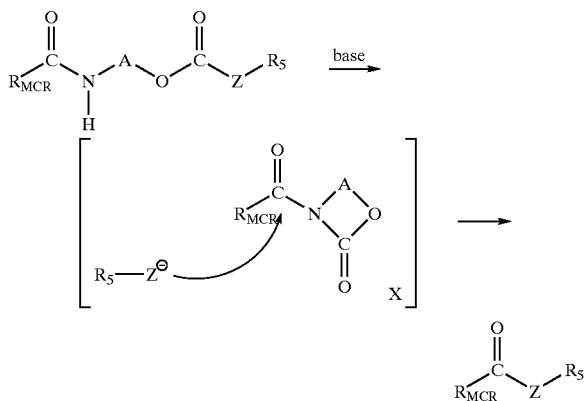

In that way it is possible to convert the secondary amide bond of the sec-amidoalkylcarbonic acid derivatives of the formulae III to IX directly into the corresponding ester. For example, by the selection of the appropriate radical R$_5$ it is possible for the carboxyl-protecting groups known from the literature [E. Haslam, *Tetrahedron* 1980, 36, 2409] to be introduced directly into the isocyanoalkylcarbonic acid derivatives in a one-pot synthesis.

As mentioned above, X is capable of being isolated when R$_5$ is a radical, such as, for example, a phenyl radical, that reduces the nucleophilicity of the Z function. As a result of its reduced nucleophilicity, caused by the aromatic mesomerism, the phenolate, for example, is not able to attack X nucleophilically and thus form the phenyl ester. This offers the possibility of isolating the corresponding primary cleavage product X and then reacting it with a nucleophile, such as an alcoholate, thiolate, hydroxyl or amino anion, for example in accordance with the following scheme, in order to obtain the corresponding esters, thioesters, amides or carboxylic acids.

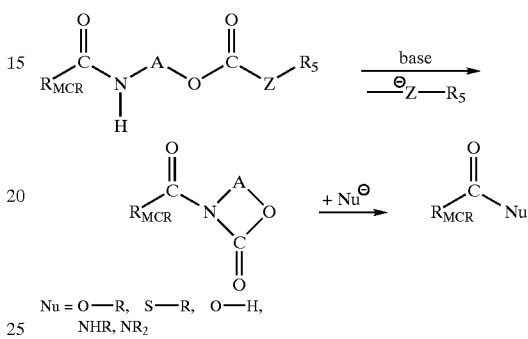

Nu = O—R, S—R, O—H, NHR, NR$_2$

Since the process according to the invention for the cleavage of secondary amide bonds also takes place under mild basic conditions, the secondary amide bonds of the sec-amidoalkylcarbonic acid derivatives may be cleaved to yield the acetidinone ring.

In summary it may be said that all sec-amidoalkylcarbonic acid derivatives that can be prepared using the novel isocyanoalkylcarbonic acid derivatives can be reacted to form the corresponding α-hydroxycarboxylic acid derivatives or α-aminocarboxylic acid derivatives, because the method of cleavage is independent of the structure of the remainder of the molecule.

Cleavage Procedure for the Sec-amidoalkylcarbonic Acid Derivatives

The sec-amidoalkylcarbonic acid derivatives of the formulae III to IX are reacted with a base. For example, the sec-amidoalkylcarbonic acid derivative is dissolved in an inert, aprotic solvent, such as, for example, THF, Et$_2$O or CH$_2$Cl$_2$, and a base, such as, for example, potassium tert-butanolate, is added. When the reaction is complete, the solvent is removed and the reaction product, which according to the structure of the radical R$_5$ and the nature of the base used may be the primary cleavage product X, an αhydroxycarboxylic acid derivative or an αaminocarboxylic acid derivative, is purified.

EXAMPLES

Example 1

Preparation of (2-Isocyano-2-methyl)-propyl-1-Carbonic Acid Allyl Ester from 4,4-dimethyl-2-oxazoline 0.1 mol of 4,4-dimethyl-2-oxazoline is dissolved in 200 ml of absolute THF and, at −78° C., 37 ml of a 2.7M n-BuLi solution are slowly added dropwise. After stirring at −78° C. for one hour, 0.1 mol of chloroformic acid allyl ester is slowly added and stirring is continued for a further 1 hour at −78° C.; the temperature of the reaction mixture is then allowed to rise slowly to 25° C. After stirring at 25° C. for one hour, the solvent is distilled off and the residue is taken up in methylene chloride and washed once with water and then with saturated sodium chloride solution. The organic phase is dried over sodium sulfate and the solvent is removed. (2-Isocyano-2-methyl)-propyl-1-carbonic acid allyl ester is obtained in a yield of 80%.

Example 2

Preparation of (1-Isocyano-2-methyl)-propyl-2-carbonic Acid Benzyl Ester from Methyl Isocyanide, Acetone and Chloroformic Acid Benzyl Ester 0.1 mol of methyl isocyanide is placed in 200 ml of absolute THF and, at −78° C., 37 ml of a 2.7M n-BuLi solution are slowly added dropwise. The mixture is stirred at −78° C. for 1 hour and then 0.1 mol of absolute acetone is slowly added. After stirring for 1 hour at −78° C., 0.1 mol of chloroformic acid benzyl ester is slowly added and stirring is continued for a further 1 hour at −78° C.; the temperature of the reaction mixture is then allowed to rise slowly to 25° C. After stirring at 25° C. for one hour, the solvent is distilled off and the residue is taken up in methylene chloride and washed once with water and then with saturated sodium chloride solution. The organic phase is dried over sodium sulfate and the solvent is removed. (1-Isocyano-2-methyl)-propyl-2-carbonic acid benzyl ester is obtained in a yield of 80%.

Example 3

Preparation of (2-Isocyano-2-methyl)-propyl-1-carbonic Acid Methyl Ester by Removal of Water from (2-Formamido-2-methyl)-propyl-1-carbonic Acid Methyl Ester 0.1 mol of (2-formamido-2-methyl)-propyl-1-carbonic acid methyl ester and 0.3 mol of triethylamine are dissolved in 300 ml of absolute methylene chloride and, at −20° C., 0.033 mol of triphosgene are added in portions. The mixture is then stirred at 0° C. for 2 hours and then at 25° C. for 1 hour. The reaction mixture is then poured into a 10% sodium hydrogen carbonate/ice-water solution and the aqueous phase is extracted three times with methylene chloride. The organic phase is dried over sodium sulfate and the solvent is removed. The crude product is purified by column chromatography over basic $Al_2O_3$, yielding (2-isocyano-2-methyl)-propyl-1-carbonic acid methyl ester in a yield of 80%.

Example 4

Preparation of from Acetic Acid, Isobutyraldehyde and (2-Isocyano-2-methyl)-propyl-1-carbonic Acid Methyl Ester by Means of P-3CR

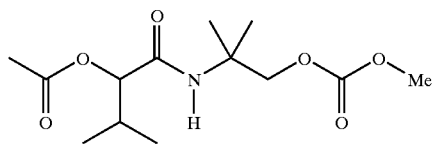

10 mmol each of acetic acid, isobutyraldehyde and (2-isocyano-2-methyl)-propyl-1-carbonic acid methyl ester are stirred in 100 ml of THF at 25° C. When the reaction is complete, the solvent is removed.
Working-up:
The residue is taken up in methylene chloride and washed with water; the organic phase is dried over magnesium sulfate and the solvent is removed. In many cases the reaction product is in the form of a pure substance after this working-up procedure. If necessary, the reaction product is purified by column chromatography.

Example 5

Preparation of from Acetic Acid, Benzylamine, Isobutyraldehyde and (2-Iso-cyano-2-methyl)-propyl-1-carbonic Acid Methyl Ester by Means of U-4CR

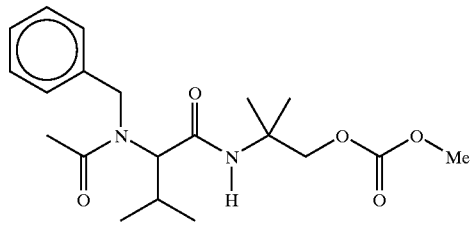

10 mmol each of benzylamine and isobutyraldehyde are placed in 100 ml of methanol, and pre-condensation is carried out at 25° C. for 1 hour, with stirring, over molecular sieve. Then 10 mmol each of acetic acid and (2-isocyano-2-methyl)-propyl-carbonic acid methyl ester are added and the mixture is stirred. When the reaction is complete, filtration is carried out over Celite and the solvent is removed. Working-up is carried out analogously to Example 4.

Example 6

Preparation of from β-Alanine, Isobutyraldehyde and (2-Isocyano-2-methyl)-propyl-1-carbonic Acid Methyl Ester by Means of U-4CR/β-AS

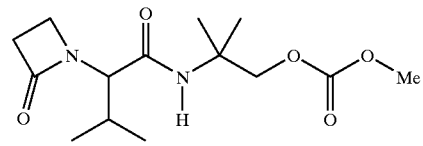

10 mmol each of β-alanine and isobutyraldehyde are placed in trifluoroethanol, and using molecular sieve pre-condensation is carried out at 25° C. for 24 hours. Then 10 mmol of (2-iso-cyano-2-methyl)-propyl-1-carbonic acid methyl ester are added and the mixture is stirred. When the reaction is complete, filtration is carried out over Celite and the solvent is removed. Working-up is carried out analogously to Example 4.

Example 7

Preparation of from Valine, Isobutyraldehyde and (2-Isocyano-2-methyl)-propyl-1-carbonic Acid Methyl Ester by Means of U-5C-4CR with Methanol as Nucleophilic Component

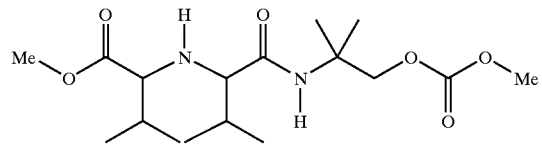

10 mmol of valine are suspended in 100 ml of methanol, and 10 mmol each of isobutyraldehyde and (2-isocyano-2- methyl)-propyl-1-carbonic acid methyl ester are added at 25° C. and the mixture is stirred. When the reaction is complete, the solvent is removed. Working-up is carried out analogously to Example 4.

Example 8

Preparation of from Valine, Isobutyraldehyde and (2-Isocyano-2-methyl)-propyl-1-carbonic Acid Methyl Ester Using the U-5C-4CR with Pyrrolidine as Nucleophilic Component

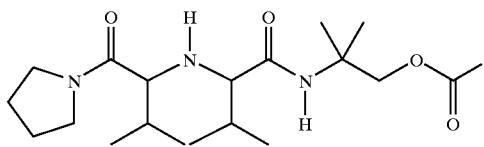

10 mmol of valine are suspended in 100 ml of tetrahydrofuran and, at 25° C., 10 mmol each of isobutyraldehyde, (2-isocyano-2-methyl)-propyl-1-carbonic acid methyl ester, pyrrolidine and then 20 ml of water are added and the mixture is stirred. When the reaction is complete, the solvent is removed. Working-up is carried out analogously to Example 4.

Example 9

Preparation of from Valine, Isobutyraldehyde and (2-Isocyano-2-methyl)-propyl-1-carbonic Acid Methyl Ester Using the U-5C-4CR with Water as Nucleophilic Component

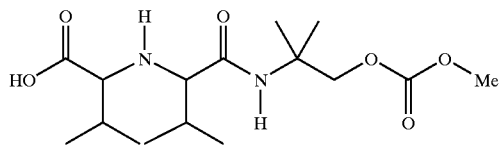

10 mmol of valine are suspended in 100 ml of a 1:1 mixture of tetrahydrofuran/water and, at 25° C., 10 mmol each of isobutyraldehyde and (2-isocyano-2-methyl)-propyl-1-carbonic acid methyl ester are added and the mixture is stirred. When the reaction is complete, the solvent is removed. Working-up is carried out analogously to Example 4.

Example 10

Cleavage of

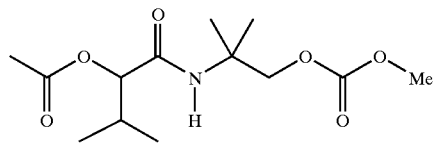

10 mmol of the above compound are dissolved in 100 ml of absolute THF. Then a solution of 10 mmol of potassium tertbutanolate in absolute THF is added dropwise at 0° C. and the mixture is stirred. When the reaction is complete, the reaction mixture is filtered over a column of silica gel.

The solvent is removed and the cleavage products are separated and purified by column chromatography, yielding

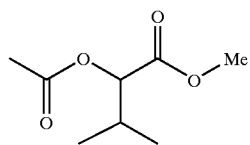

in a yield of 80%.

Example 11

Cleavage of

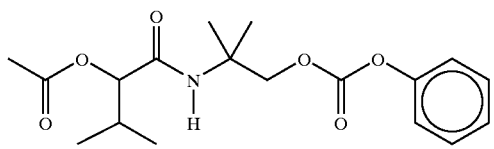

10 mmol of the above compound are dissolved in 100 ml of absolute THF. Then a solution of 10 mmol of potassium tertbutanolate in absolute THF is added dropwise at 0° C. and the mixture is stirred. When the reaction is complete, the reaction mixture is filtered over a column of silica gel. The solvent is removed and the cleavage products are separated and purified by column chromatography, yielding

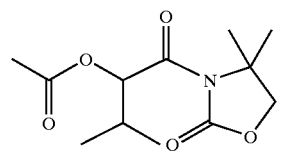

in a yield of 80%.

What is claimed is:

1. A compound of the formula VIII

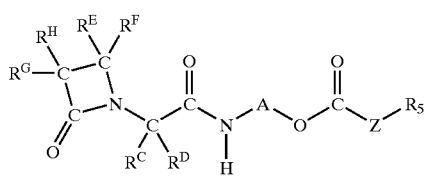

VIII wherein A is group of the formula

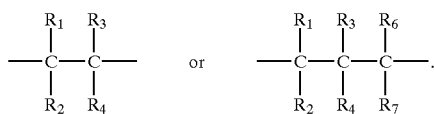

Z is an O or S atom, $R_1$ to $R_4$ and, when present, $R_6$ and $R_7$ each have a maximum of 20 carbon atoms and are independently of one another H atoms, substituted or unsubstituted alkyl, alkenyl, alkynyl, alkaryl, aryl, alicyclic radicals, heteroalicyclic or heteroaryl radicals having up to 4 hetero atoms O, N, S, and optionally two of the radicals $R_1$ to $R_4$ and, when present, $R_6$ and $R_7$ that are separated from one another by up to two carbon atoms are constituents of a common ring system, the ring system comprising a substituted or unsubstituted alicyclic monocycle having 5 to 8 ring atoms, a heteroalicyclic monocycle having 5 to 8 ring atoms with up to two hetero atoms O, N, S, an alicyclic bicycle having 7 to 14 ring atoms, or a heteroalicyclic bicycle having 7 to 14 ring atoms with up to 4 hetero atoms O, N, S, and $R_5$ has a maximum of 20 carbon atoms and is a substituted or unsubstituted alkyl, alkenyl, alkynyl, allyl, alkaryl, aryl, alicyclic radical, heteroalicyclic or heteroaryl radical having up to 4 hetero atoms O, N, S, and the radicals $R^C$, $R^D$, $R^E$, $R^F$, $R^G$, $R^H$, each have a maximum of 20 carbon atoms and are independently of one another H atoms or unsubstituted alkyl, alkenyl, alkynyl, alkaryl, aryl, alicyclic radicals, heteroalicyclic or heteroaryl radicals having up to 6 hetero atoms O, N, S or are corresponding radicals that are substituted by one, two or more halogen, tert-amino, nitro, cyano, carboxylic acid ester, carboxylic acid amide, carboxylic acid imide, alkyloxy, epoxy, boron, silyloxy, silyl, thio, sulfonic acid ester, sulfenic acid ester, sulfinic acid ester, sulfonamido, urethane or urea functions.

2. The compound according to claim 1, wherein they are bonded to a solid phase via one or more of the radicals $R_1$ to $R_4$ and, when present, $R_6$ and $R_7$, also $R_5$ or Z.

3. Process for the preparation of compounds of the formula VIII according to claim 1, wherein a β-amino acid of the formula $H_2N$—$CR^ER^F$—$CR^GR^H$—COOH is reacted with a carbonyl component $R^C$—CO—$R^D$ and the isocyanoalkylcarbonic acid derivative of formula I in an Ugi 4-component reaction.

4. The compound according to claim 1, wherein the substituents of $R_1$ to $R_7$ are one, two, three or more halogen, tert-amino, nitro, ether, silyloxyalkyl, thioether, carboxylic acid ester, tert-carboxylic acid amide, carboxylic acid imide, silyl, sulfonic acid ester, sulfenic acid ester, sulfinic acid ester, or tert-sulfonamido functions.

5. The compound according to claim 1, wherein A is a group of the formula —$C(CH_3)_2$—$CH_2$—.

* * * * *